United States Patent [19]

Haas et al.

[11] 4,013,708
[45] Mar. 22, 1977

[54] ARYLCHALCOGENO-SUBSTITUTED ALIPHATIC ACIDS AND ESTERS

[75] Inventors: Georges Haas, Oberwil; Pier Giorgio Ferrini, Binningen; Alberto Rossi, Oberwil, all of Switzerland

[73] Assignee: Ciba-Geigy Corporation, Ardsley, N.Y.

[22] Filed: Sept. 11, 1974

[21] Appl. No.: 505,111

[30] Foreign Application Priority Data

Sept. 18, 1973 Switzerland ............. 13387/73
Sept. 18, 1973 Switzerland ............. 13389/73

[52] U.S. Cl. ............. 260/473 G; 260/294.8 G; 260/295 R; 260/399; 260/405.5; 260/410; 260/410.9 R; 260/413; 260/465 F; 260/465 G; 260/465 K; 260/465 R; 260/470; 260/505 C; 260/512 C; 260/516; 260/520 C; 260/556 HR; 260/558 S; 260/559 B; 260/564 R; 424/263; 424/304; 424/308; 424/315; 424/317; 424/321; 424/324; 424/326

[51] Int. Cl.² ............. C07C 65/00; C07C 65/14; C07C 69/76

[58] Field of Search ......... 260/473 G, 520 C, 470, 260/516, 399, 410, 410.9 R, 413

[56] References Cited

UNITED STATES PATENTS

| | | | |
|---|---|---|---|
| 3,452,081 | 6/1969 | Sprague et al. ............. | 260/473 |
| 3,646,122 | 2/1972 | Bencze ............. | 260/520 |
| 3,658,829 | 4/1972 | Nakamura et al. ............. | 260/520 X |
| 3,679,800 | 7/1972 | Bencze ............. | 260/520 X |

FOREIGN PATENTS OR APPLICATIONS 2,060,573  6/1971  Germany

Primary Examiner—Lewis Gotts
Assistant Examiner—Dolph H. Torrence
Attorney, Agent, or Firm—Joseph G. Kolodny; Theodore O. Groeger; John J. Maitner

[57] ABSTRACT

New compounds of the general formula I $$R_1 - Ph - X - CR_2R_4 - alk - R_3 \qquad (I)$$

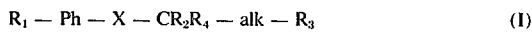

wherein $R_1$ denotes a cycloalkenyl radical or a monocyclic cycloalkyl radical, Ph denotes an optionally substituted phenylene radical, X denotes the oxy or thio group, $R_2$ denotes hydrogen or alkyl, $R_3$ denotes an optionally functionally modified carboxyl group, a sulpho group or a sulphamido group, alk denotes an alkylene or alkenylene radical which separates the groups $R_1$—Ph—X—$CR_2R_4$ and $R_3$ by at least 2 carbon atoms and $R_4$ is hydrogen or, if alk separates the groups $R_1$—Ph—X—$CR_2R_4$ and $R_3$ by at least 3 carbon atoms or $R_1$ denotes a cycloalkenyl radical, $R_4$ can also denote alkyl, in the free form or in the form of salts are useful as antiallergics.

14 Claims, No Drawings

ARYLCHALCOGENO-SUBSTITUTED ALIPHATIC ACIDS AND ESTERS

The invention relates to new compounds of the general formula I

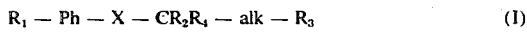

wherein $R_1$ denotes a cycloalkenyl radical or a monocyclic cycloalkyl radical, Ph denotes an optionally substituted phenylene radical, X denotes the oxy or thio group, $R_2$ denotes hydrogen or alkyl, $R_3$ denotes an optionally functionally modified carboxyl group, a sulpho group, a sulpho group or a sulphamido group, alk denotes an alkylene or alkenylene radical which separates the groups $R_1$—Ph—X—$CR_2R_4$ and $R_3$ by at least 2 carbon atoms and $R_4$ is hydrogen, or, if alk separates the groups $R_1$—Ph—X—$CR_2R_4$ and $R_3$ by at least 3 carbon atoms and $R_1$ denotes a cycloalkenyl radical, $R_4$ can also denote alkyl, in the free form or in the form of salts, processes for the manufacture of the new compounds and pharmaceutical preparations containing the new compounds.

Cycloalkenyl $R_1$ can be poly-unsaturated but is preferably mono-unsaturated, the double bond starting in particular from the C atom bonded to the radical Ph, and can contain several rings, in particular 2 rings, but is preferably monocyclic. Bicyclic cycloalkenyl $R_1$ preferably contains rings with 5–7 ring members which have 1–4, preferably 2 or 3, carbon atoms in common. As examples there may be mentioned optionally lower-alkylated 2- and 3-bicyclo[4,4,0]dec-2-enyl, 2-bicyclo[2,2,2]oct-2-enyl, 2-bornenyl and 2-norbornenyl.

"Lower" is here and in the subsequent text used to designate those alkyl radicals, and groups derived from these radicals, which contain not more than 7 carbon atoms.

Examples of lower alkyl radicals are methyl, ethyl, propyl or isopropyl radicals or straight or branched butyl, pentyl, hexyl or heptyl radicals which are bonded in any desired position.

Monocyclic cycloalkyl and cycloalkenyl radicals $R_1$ above all contain 4 to 12, and preferably 5 to 8, ring members, such as, for example, optionally lower-alkylated cyclobutyl, cyclodecyl, cyclodecyl or preferably optionally lower-alkylated 1-cyclobutenyl, 1-cyclododecenyl, cyclooctyl, cycloheptyl, cyclohexyl or cyclopentyl or especially optionally lower-alkylated, but above all unsubstituted, 1-cyclooctenyl, 1-cycloheptenyl, 1-cyclohexenyl or 1-cyclopentenyl.

The optionally substituted phenylene radical Ph is an o-, m- or preferably p-phenylene radical and can carry one or more substituents, such as lower alkyl radicals and/or alkoxy radicals, for example the lower alkyl radicals mentioned or lower alkoxy radicals derived therefrom, halogen atoms, for example fluorine, bromine or especially chlorine atoms, and/or trifluoromethyl groups and/or nitro groups.

The alkylene or alkenylene radical $CR_2R_4$-alk contains up to 20, such as 4 to 11, and preferably 4 to 7, carbon atoms and can be straight-chain or be branched at one or several points, with at least one side chain starting preferably from the carbon atom in the α-position to the group X and one of the optionally present double bonds preferably starting from the carbon atom in the α-position to the group $R_3$. Preferred alkylene or alkenylene radicals alk are, for example, ethylene and 1,3-propylene.

The optionally functionally modified carboxyl group $R_3$ is, for example, the nitrile, amidino or hydroxyamino-carbonyl group, or an amidised or, in particular, a free or esterified carboxyl group.

Esterified carboxyl groups are in particular those esterified with aliphatic, cycloaliphatic or araliphatic alcohols. Ester-forming alcohols which can be used are, in particular, lower alkanols which contain up to 7 C atoms and can be straight-chain or branched-chain, such as, for example, methanol, ethanol, n-propanol, isopropanol, butanols, hexanols or heptanols, cycloalkanols which contain 4 to 8 C atoms, preferably 5 or 6 C atoms, in the ring and which can be substituted by lower alkyl, such as, for example, cyclopentanol or cyclohexanol, and phenyl-lower alkanols of which the phenyl radical is unsubstituted or can contain one or more substituents, such as lower alkyl, lower alkoxy, halogen or trifluoromethyl, and of which the lower alkanol part has the abovementioned meaning, for example benzylalcohols or 2-phenylethanol.

Further ester-forming alcohols which can be used are those of the formula HO—Q—Py, wherein Q denotes an alkylene radical or a direct bond and Py denotes a pyridyl radical. Alkylene radicals Q are straight-chain or branched-chain lower alkylene radicals with 1 to 3 C atoms in the alkylene chain, preferably those with a total of 1 to 4 C atoms, such as 1,1-or 2,2-butylidene, 1,1-isobutylidene, 1,2-propylene or especially propylidene, isopropylidene, ethylidene, ethylene or methylene.

In the amidised carboxyl groups (carbamoyl groups) the amide nitrogen atom can be unsubstituted, monosubstituted or disubstituted, for example by preferably lower radicals, for example radicals possessing at most 8 carbon atoms, of aliphatic character, which can also be interrupted by heteroatoms, such as oxygen atoms or sulphur atoms.

Examples of amide substituents which may be mentioned are alkyl, alkenyl, cycloalkyl, cycloalkylalkyl or alkylene radicals which can also be interrupted by oxygen atoms or sulphur atoms, and also phenylalkyl.

Possible amide substituents are in particular: lower alkyl radicals, such as methyl, ethyl, n-propyl, isopropyl and straight or branched butyl, pentyl, hexyl or heptyl bonded in any desired position, lower alkenyl radicals, such as, for example allyl or methallyl, lower alkylene radicals such as, for example, butylene-(1,4), pentylene-(1,5), hexylene-(1,6) or heptylene-(2,6), cycloalkyl with 4 to 8 C atoms, preferably 5 or 6 C atoms in the ring, such as, for example, cyclopentyl or cyclohexyl, cycloalkylalkyl, especially cycloalkyl-lower alkyl, for example cyclohexylmethyl, or corresponding radicals interrupted by the hetero-atoms mentioned, such as, for example, lower alkoxyalkyl or alkylmercaptoalkyl radicals, such as, for example, 2-methoxyethyl, 2-ethoxyethyl, 3-methoxypropyl or 2-methylmercaptoethyl, or oxaalkylene or thiaalkylene radicals, such as 3-oxapentylene-(1,5) or 3-thiapentylene-(1,5), or 1,5-dimethyl-3-thiapentylene-(1,5), or phenylalkyl radicals, especially phenyl-lower alkyl radicals, which can be unsubstituted or monosubstituted or polysubstituted in the phenyl part and wherein possible substituents are above all lower alkyl, lower alkoxy, halogen or trifluoromethyl, such as benzyl or 2-phenylethyl.

The amino group of the amidised carboxyl group (carbamoyl group) is, in particular, a free, mono-lower alkylated or di-lower alkylated amino group, or an optionally C-lower alkylated pyrrolidino, piperidine, morpholino or thiomorpholino group.

A sulphonamido group is preferably a sulphonamido group monosubstituted by lower alkyl or phenyl-lower alkyl, wherein lower alkyl and phenyl-lower alkyl have the above meaning, for example the N-methylsulphonamido, N-ethylsulphonamido, N-benzylsulphonamido or N-(α-phenethyl)-sulphonamido group, and wherein phenyl groups which may be present can be unsubstituted or monosubstituted or polysubstituted and possible substituents are lower alkyl, lower alkoxy, halogen or trifluoromethyl. The sulphamoyl group should be singled out particularly as a sulphonamido group.

The new compounds possess valuable pharmacological properties, above all a histamine release-inhibiting action, as can be shown in vitro in doses of about 0.005 to 0.050 mg/ml in the histamine release test on suspensions of peritoneal cells of rats, using [D-Ser$^1$,Lys$^{17,18}$]-β-corticotropin-(1-19)-nonadecapeptide tetradecyl ester hexaacetate [R. Jaques and M. Brugger, Pharmacology 2, 361–370, (1969); M. Brugger, Helv. chim. acta 54, 1261-1274, (1971)]. Equally, they show an inhibiting action on anaphylactic reactions, as can be shown, for example, in vitro in doses of 0.001 to 0.010 mg/ml in the Schultz-Dale reaction on the contraction, triggered by ovalbumin, of a piece of intestine from an active-sensitised guinea pig.

The new compounds are therefore useful as antiallergic agents.

Above all, the invention relates to those compounds of the formula I, wherein $R_1$ denotes a cycloalkyl or 1-cycloalkenyl radical with 4 to 12, for example 5 to 8, ring members, Ph denotes an o-, m- or above all p-phenylene which is optionally monosubstituted or polysubstituted by alkyl and/or alkoxy radicals, for example lower alkyl and/or alkoxy radicals, halogen atoms, for example fluorine, bromine and/or chlorine, and/or the trifluoromethyl group and/or the nitro group, X denotes the oxy group or the thio group, $CR_2R_4$-alk denotes an alkylene or alkenylene radical with 4 to 20 C atoms which separates the groups X and $R_3$ by at least 4 C atoms, and $R_3$ denotes an optionally functionally modified carboxyl group, the sulpho group or sulphonamido group, or $R_2$ denotes hydrogen or lower alkyl with 1 to 4 C atoms, alk denotes a radical $CHR_5$-$CHR_6$, wherein $R_5$ and $R_6$ independently of one another denote hydrogen or lower alkyl with 1 to 4 C atoms or $R_5$ and $R_6$ conjointly represent an additional bond, $R_4$ is hydrogen or, if $R_1$ is a cycloalkenyl radical, can also denote lower alkyl, and $R_3$ denotes the nitrile, amidino or hydroxyaminocarbonyl group, a sulphonamido group or an amidised or esterified carboxyl group or especially the free sulpho or carboxyl group.

Above all, the invention relates to those compounds of the formula I, wherein $R_1$ denotes a cycloalkyl or 1-cycloalkenyl radical with 5 to 8 ring members, Ph denotes o-, m- or especially p-phenylene which is optionally substituted by lower alkyl or alkoxy, such as methyl or methoxy, or halogen, such as chlorine, X denotes the oxy or thio group, $CR_2R_4$-alk separates the groups X and $R_3$ by 4 to 11 C atoms and denotes an alkylene or alkenylene radical with 4 to 11 C atoms which is optionally branched, preferably once, in the α-position to the group X, and $R_3$ denotes a sulphonamido group, the sulpho group, the amidino group, the hydroxyamino group, the nitrile group, an amidised or, particularly, an esterified carboxyl group or, especially, the free carboxyl group.

The invention equally relates above all to those compounds of the formula I, wherein $R_1$ denotes a cycloalkyl or 1-cycloalkenyl radical with 5 to 8 ring members, Ph denotes phenylene which is optionally monosubstituted or polysubstituted by lower alkyl, such as methyl, lower alkoxy, such as methoxy, and/or halogen, such as bromine, fluorine or above all chlorine, X denotes the oxy or thio group, $R_2$ denotes hydrogen or lower alkyl with 1 to 4 C atoms, alk denotes a radical $CHR_5$-$CHR_6$, wherein $R_5$ and $R_6$ independently of one another denote hydrogen or lower alkyl with 1 to 4 C atoms or $R_5$ and $R_6$ conjointly represent an additional bond, $R_4$ is hydrogen or, if $R_1$ is a cycloalkenyl radical, can also denote lower alkyl with 1 to 4 C atoms and $R_3$ denotes the nitrile group, a sulphonamido group which is monosubstituted by lower alkyl or phenyl-lower alkyl, the free carbamoyl group or a mono-or di-lower alkylated carbamoyl group, a carboxyl group which is esterified with a lower alkanol, cycloalkanol or phenyl-lower alkanol or especially the free sulpho group or carboxyl group.

Very particularly, the invention relates to those compounds of the formula I, wherein $R_1$ denotes a cycloalkyl or 1-cycloalkenyl radical with 5 to 8 ring members, Ph denotes p-phenylene which is optionally monosubstituted, especially in the o-position to $R_1$, by methyl, methoxy or chlorine, X denotes the oxy or thio group, $CR_2R_4$-alk separates the groups X and $R_3$ by 4 to 7 C atoms and denotes alkylene with 4 to 11 C atoms which is optionally branched once in the α-position to the group X, or denotes alkenylene with 4 to 11 C atoms which is optionally branched once in the α-position to the group X and of which the double bond starts from the C atom bonded to the group $R_3$, and $R_3$ denotes the sulpho group, the nitrile group, a carbamoyl group which is optionally substituted by hydrocarbon radicals of aliphatic character having up to 8 C atoms, or especially a carboxyl group which is optionally esterified by a lower alkanol, cycloalkanol or phenylalkanol but above all the free carboxyl group.

Equally, the invention relates very particularly to those compounds of the formula I, wherein $R_1$ denotes a cycloalkyl or 1-cycloalkenyl radical with 5 to 8 C atoms, Ph denotes phenylene which is optionally monosubstituted by lower alkyl, such as methyl, lower alkoxy, such as methoxy, or halogen, especially chlorine, $R_2$ denotes hydrogen or lower alkyl, alk denotes a radical $CHR_5$-$CHR_6$, $R_4$, $R_5$ and $R_6$ denote hydrogen or $R_4$ denotes hydrogen and $R_5$ and $R_6$ conjointly represent an additional bond and $R_3$ denotes the nitrile group, a monolower alkylated sulphonamido group, an optionally mono- or di-lower alkylated carbamoyl group, a lower alkoxycarbonyl group or especially the free sulpho or carboxyl group.

Above everything else, the invention relates to those compounds of the formula I, wherein $R_1$ denotes 1-cyclooctenyl, cyclooctyl, 1-cycloheptenyl, cycloheptyl, 1-cyclohexenyl, cyclohexyl, 1-cyclopentenyl or cyclopentyl, Ph denotes p-phenylene which is optionally monosubstituted by methyl, methoxy or chlorine, X denotes the oxy group, $CR_2R_4$-alk separates the groups X and $R_3$ by 4 to 7 carbon atoms and denotes alkylene with 4 to 7 C atoms which is optionally branched once in the α-position to the group X but is preferably unbranched, or denotes unbranched alkenylene with 4 to 7 C atoms of which the double bond starts from the C atom in the α-position to the group $R_3$, and $R_3$ denotes the sulpho group or a carboxyl group which is optionally esterified with a lower alkanol, such as ethanol, but above all a free carboxyl group.

Above everything else, the invention also relates to those compounds of the formula I, wherein $R_1$ denotes cyclooctyl, cycloheptyl or cyclohexyl, cyclopentyl or 1-cyclooctenyl, 1-cycloheptenyl, 1-cyclohexenyl or 1-cyclopentenyl, Ph denotes o- or above all m- or p-phenylene which is optionally monosubstituted by methoxy, methyl or chlorine, X denotes the oxy or thio group, $R_2$ and $R_4$ denote hydrogen, alk denotes ethylene and $R_3$ denotes a carboxyl group which is esterified with a lower alkanol with 1 to 4 C atoms or especially denotes the free sulpho group or carboxyl group.

Especially, the invention relates to those compounds of the formula I, wherein $R_1$ denotes cyclooctyl, 1-cyclooctenyl, cycloheptyl, 1-cycloheptenyl, cyclohexyl or 1-cyclohexenyl, Ph denotes p-phenylene, X denotes the oxy group, $CR_2R_4$-alk denotes an unbranched alkylene radical or an alkenylene radical which is mono-unsaturated in the α-β-position to the group $R_3$, which separates the groups X and $R_3$ by 4 to 7 C atoms, and $R_3$ denotes the sulpho group, a carboxyl group which is optionally esterified with a lower alkanol with 1 to 4 C atoms but above all the free carboxyl group, and specifically 5-[p(1-cyclootenyl)-phenoxy]-n-valeric acid, 5-[p-(1-cyclooctenyl)-phenoxy]-n-valeric acid ethyl ester, 5-(p-cyclootylphenoxy)-n-valeric acid and 5-(p-cyclooctylphenoxy)-n-valeric acid ethyl ester.

Especially, however, the invention relates to those compounds of the formula I, wherein $R_1$ denotes 1-cyclooctenyl, 1-cycloheptenyl, cycloheptyl, 1-cyclohexenyl or cyclohexyl, Ph denotes unsubstituted m- or p-phenylene, X denotes the oxy or thio group, $R_2$ and $R_4$ denote hydrogen alk denotes ethylene and $R_3$ denotes the free sulpho or carboxyl group, and specifically 3-[p-(1-cyclohexenyl)-phenoxy]-propanesulphonic acid, 3-[p-(1-cyclohexenyl)-phenylthio]-propanesulphonic acid, 4-[p-(1-cyclohexenyl)-phenoxy]-butyric acid, 4-[p-(1-cyclooctenyl)-phenoxy]-butyric acid and 4-(m-cyclohexylphenoxy)-butyric acid.

The new compounds can be manufactured according to methods which are in themselves known.

Preferably, the new compounds of the formula I are manufactured by reacting a compound of the formula II

$$R_1 - Ph - X' \qquad (II)$$

wherein $R_1$ and Ph have the abovementioned meaning and X' represents a free hydroxyl or mercapto group, with a compound of the formula III

$$Z - CR_2R_4 - alk - R_3 \qquad (III)$$

wherein $R_2$, $R_4$, alk and $R_3$ have the abovementioned meanings and Z represents a reactive esterified hydroxyl group.

A reactive esterified hydroxyl group Z is in particular a hydroxyl group esterified with a hydrogen halide acid, for example hydrochloric acid or above all hydrobromic acid, or sulphuric acid, or a lower alkenesulphonic acid or benzenesulphonic acid, for example methanesulphonic acid, ethanesulphonic acid or p-toluenesulphonic acid, or a hydroxyl group which is esterified by the radical $R_3$ which optionally represents the sulpho group, to form the corresponding sultone formed by the hydroxy compound derived from the compound of the formula III. In this reaction, the starting materials are preferably compounds of the formula III, wherein $R_3$ is preferably the nitrile group or an esterified or amidised carboxyl group, and the phenol or thiophenol of the formula II is preferably employed as a salt, especially as an alkali metal salt, for example the sodium salt or potassium salt. An example of a preferred embodiment is to react a suitable bromoester of the formula III with the sodium salt of a phenol or thiophenol of the formula II. The reaction can be carried out in the usual manner, in particular in an inert, preferably anhydrous, solvent, and/or at elevated temperature, and/or in the presence of a strong base, for example an alkanolate, above all an alkali metal alkanolate, such as a sodium alkanolate or potassium alkanolate, for example sodium ethylate or sodium methylate.

Compounds of the formula I which are branched in the α-position to $R_3$ can also be manufactured by reacting a compound of the formula IV

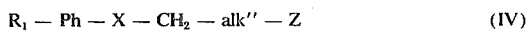

$$R_1 - Ph - X - CH_2 - alk'' - Z \qquad (IV)$$

wherein $R_1$, Ph and X have the indicated meanings, alk'' denotes an alkylene or alkenylene radical which possesses two hydrogen atoms in the α-position to Z and Z denotes a reactive esterified hydroxyl group, such as one of those mentioned for the starting materials of the formula III, with and α-metal salt of a compound of the formula V

$$H - CR_7R_8 - R_3'' \qquad (V)$$

wherein $R_7$ denotes alkyl, $R_8$ denotes alkyl or, as a second choice, hydrogen and $R_3''$ denotes a carboxyl group which is present in the form of a metal salt or is esterified or amidised.

The reaction can be carried out in the usual manner, for example in an inert solvent, such as an ether, for example in tetrahydrofurane, advantageously by forming the α-metal salt, for example the alkali metal salt, of the compound of the formula V in situ, for example by reaction with a metal compound of a hydrocarbon or secondary amine, for example with butyl-lithium or diisopropylamine-sodium.

In resulting compounds, substituents can be introduced, modified or split off, within the scope of the end products.

Thus, for example, in resulting compounds wherein $R_3$ represents an optionally modified carboxyl group, such as, for example, a free, amidised or esterified carboxyl group, or the nitrile, amidino or hydroxyaminocarbonyl group, the radicals $R_3$ can be converted into one another.

Functionally modified, for example esterified and amidised carboxyl groups, nitrile, amidino and hydroxyaminocarbonyl groups can be converted to free carboxyl groups in the usual manner, for example by hydrolysis, preferably in the presence of a strong base or strong acid, such as an alkali metal hydroxide, for example sodium hydroxide or potassium hydroxide, or of a mineral acid, for example of sulphuric acid, phosphoric acid or hydrochloric acid, hydrobromic acid or hydriodic acid, or of an organic acid, for example of a lower alkanecarboxylic acid, say of acetic acid, or of an organic sulphonic acid, for example benzenesulphonic acid, toluenesulphonic acid, p-bromobenzenesulphonic acid, ethanesulphonic acid, ethenesulphonic acid or methanesulphonic acid. If desired, oxidising agents, such as nitrous acid, can be added when hydrolysing the carbamoyl group.

Free or esterified carboxyl groups can also be converted in the usual manner into amidised carboxyl groups, for example by reaction with ammonia or with amines which have at least one hydrogen atom on the nitrogen atom and, optionally, dehydration of the ammonium salt produced as an intermediate, for example with phosphorus pentoxide.

Unsubstituted carbamoyl groups can be converted into nitrile groups in the usual manner, for example by dehydration, preferably with phosphorus pentoxide.

Free carboxyl groups can be esterified in the usual manner, for example by reaction with a corresponding alcohol, advantageously in the presence of an acid, such as a mineral acid, for example sulphuric acid or hydrochloric acid, or in the presence of a water-binding agent, such as dicyclohexylcarbodiimide, or by reaction with a corresponding diazo compound, for example a diazoalkane. The esterification can also be carried out by reaction of a salt of the acid, for example the sodium salt, with a reactive esterified alcohol, for example a halide, such as a chloride.

Free carboxyl groups can, for example, also be converted into acid halide groupings or acid anhydride groupings in the usual manner, for example by reaction with halides of phosphorus or sulphur, such as thionyl chloride, phosphorus pentachloride or phosphorus tribromide, or with acid halides, such as chloroformic acid esters. The acid anhydride and acid halide groups can then be converted into esterified carboxyl groups or carbamoyl groups in the usual manner, respectively by reaction with corresponding alcohols, if desired in the presence of acid-binding agents, such as organic or inorganic bases, or by reaction with ammonia or amines.

Further, sulpho groups and sulphonamido groups can be converted into one another in compounds obtained.

Sulphonamido groups can be converted to the free sulpho group in the usual manner, for example by hydrolysis, preferably in the presence of strong acids or bases, for example hydrochloric acid or potassium hydroxide.

The free sulphonamido group can be monoalkylated in a manner which is in itself known, for example with reactive esterified lower alkanols, for example with di-lower alkyl sulphates, such as dimethyl sulphate, preferably in the presence of strong bases, for example sodium hydroxide.

Furthermore, substituents of Ph can be introduced, modified or removed in compounds obtained wherein Ph represents a substituted or unsubstituted phenylene radical.

Thus, halogenation, such as chlorination or bromination, can be carried out in the usual manner, for example with N-chlorosuccinimide or with free chlorine or bromine, if necessary with cooling and/or in the presence of a catalyst, such as, for example, iron-III chloride, aluminium chloride or the corresponding bromides.

On the other hand, halogen, for example bromine, which is present can be removed hydrogenolytically, for example with hydrogen in the presence of a catalyst, such as palladium or Raney nickel, or with triethyltin hydride.

Equally, nitro groups can be introduced in the usual manner, especially by nitration, for example with a mixture of nitric acid and sulphuric acid.

Further, trifluoromethyl groups can be introduced into a radical Ph, for example by means of trifluoromethyl iodide, using copper powder.

Furthermore, resulting compounds of the formula I which carry at least one hydrogen atom in the $\alpha$-position to $R_3$ can be $\alpha$-alkylated, especially by reaction with a reactively esterified lower alkanol, such as a lower alkyl halide, for example methyl iodide or 1-n-heptyl bromide in which case the compound is first $\alpha$-metallised, that is to say the $\alpha$-hydrogen atom is replaced in the usual manner by a metal, such as an alkali metal, for example sodium or lithium, using, for example, metal hydrides, amides or alkyls, preferably alkali metal hydrides, amides or alkyls, for example sodium amide, sodium hydride, lithium N,N-diisopropylamide or butyl-lithium, as the metallising agents.

Furthermore, in resulting compounds wherein $CR_2R_4$-alk denotes an alkenylene radical, the latter can be reduced in the usual manner to a corresponding alkylene radical, for example by catalytic hydrogenation, such as by hydrogen in the presence of a hydrogenation catalyst, for example sulphidised Raney nickel. Equally, a cycloalkenyl radical, especially 1-cycloalkenyl radical, $R_1$ in resulting compounds can also be reduced to a cycloalkyl radical, for example by catalytic hydrogenation as indicated above.

In the abovementioned reductions care must be taken, where relevant, that further reducible groups are not attacked. Thus care must be taken particularly in the case of the reduction with Raney nickel and hydrogen that halogen atoms which may be present and are bonded to aromatic rings are not replaced by hydrogen. In addition, attention must be given in all the reductions, especially catalytic reductions, to a double bond which may be present in the radical $R_1$ and/or $CR_2R_4$-alk. Preferably, suitable catalysts should be used and the hydrogen absorption should be followed volumetrically and the hydrogenation discontinued when the calculated amount has been absorbed.

The reactions mentioned can optionally be carried out simultaneously or successively, and in any desired sequence.

The reactions mentioned are carried out in the usual manner, in the presence or absence of diluents, condensation agents and/or catalytic agents, at lowered, ordinary or elevated temperature, and if appropriate in a closed vessel.

Depending on the process conditions and starting materials, end products which can form salts are obtained in the free form or in the form of their salts, which can be converted in the usual manner into one another or into other salts. Thus, acid end products, for example those in which a free carboxyl group of the sulpho group is present, are obtained in the free form or in the form of their salts with bases. Resulting free acid compounds can be converted in the usual manner, for example by reaction with corresponding basic agents, into the salts with bases, above all into therapeutically usable salts with bases, for example salts with organic amines, or metal salts. Possible metal salts are above all alkali metal salts or alkaline earth metal salts, such as sodium salts, potassium salts, magnesium salts or calcium salts. Free acids can be liberated from the salts in the usual manner, for example by reaction with acid agents.

These and other salts can also be used for purifying the new compounds, for example by converting the free compounds into their salts, isolating these and again converting them into the free compounds. Because of the close relationships between the new compounds in the free form and in the form of their salts, the free compounds are, in the preceding and following text, where appropriate also to be understood as the corresponding salts, with respect to general sense and intended use.

The invention also relates to those embodiments of the process according to which a compound obtainable as an intermediate product at any stage of the process is used as the starting material and the missing process steps are carried out, or the process is discontinued at any stage, or in which a starting material is formed under the reaction conditions or in which a reactant is present in the form of its salts, if appropriate.

Depending on the choice of the starting materials and procedures, the new compounds can be in the form of one of the various stereoisomers or of a stereoisomer mixture, for example as geometric isomers, that is to say cis-trans isomers and, depending on the number of asymmetrical carbon atoms, as optical antipodes or racemates or as isomer mixtures, for example as mixtures of geometrical isomers or racemate mixtures.

Resulting isomer mixtures (racemate mixtures) can be separated into the two stereoisomeric, for example diastereomeric, pure isomers, for example racemates, on the basis of the physico-chemical differences of the constituents, in a known manner, for example by chromatography and/or fractional crystallisation.

Resulting racemates can be separated into the optical antipodes according to known methods, for example by recrystallisation from an optically active solvent, with the aid of micro-organisms, or by reaction of a free carboxylic acid with an optically active base which forms salts with the racemic compound and separation of the salts obtained in this manner, for example on the basis of their different solubilities, into the diastereomers, from which the antipodes can then be liberated by treatment with suitable agents. Particularly customary optically active bases are, for example, (−)-brucine, (+)-quinidine, (−)-quinine, (+)-cinchonine, (+)-dehydroabietylamine, (+)- and (−)-ephedrine, (+)- and (−)-1-phenyl-ethylamine or their N-monoalkylated or dialkylated derivatives. Advantageously, the more active of the two antipodes is isolated.

The starting materials are known or can, if they are new, be manufactured according to methods which are in themselves known.

The starting materials of the formula II, wherein X' denotes the mercapto group, can be manufactured, for example, by reacting a ketone, derived from a cycloalkane or from a cycloalkene which is unsaturated in a position other than the α,β-position, with a halogenophenyl-Grignard compound produced from a dihalogenobenzene, for example dibromobenzene, and eliminating water. The resulting cycloalk(en)ylphenyl halide is in turn used to produce a Grignard compound, for example with magnesium, and this compound is treated with sulphur and after customary working up gives the desired thiophenol.

The starting materials of the formula III can be obtained, for example, by esterification of the corresponding hydroxy-alkane- or -alkene-carboxylic acid derivatives or -sulphonic acid derivatives.

The pharmacologically usable compounds of the present invention can be used, for example, for the manufacture of pharmaceutical preparations which contain an effective amount of the active substance together with, or mixed with, inorganic or organic, solid or liquid, pharmaceutically usable excipients which are suitable for enteral, parenteral or topical administration. Preferably, tablets or gelatine capsules are used, which contain the active compound together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycols; tablets also contain binders, for example magnesium silicate, starches, such as maize starch, wheat starch, rice starch or arrowroot, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, enzymes for the binders and/or effervescent mixtures, or adsorbents, dyestuffs, flavouring substances and sweeteners. Injectable preparations are preferably isotonic aqueous solutions or suspensions, and suppositories or ointments are above all fat emulsions or fat suspensions. The pharmacological preparations can be sterilised and/or contain auxiliaries, for example preservatives, stabilisers, wetting agents and/or emulsifiers, solubilising agents, salts for regulating the osmotic pressure and/or buffers. The present pharmaceutical preparations which can, if desired, contain further pharmacologically valuable materials are manufactured in a manner which is in itself known, for example by means of conventional mixing, granulating or dragee-making processes and contain from about 0.1% to about 75%, in particular from about 1% to about 50%, of the active compound.

EXAMPLE 1

13 g of p-(1-cyclooctenyl)-phenol are added to a solution of 1.8 g of sodium in 65 ml of absolute ethanol whilst stirring in an anhydrous atmosphere, and after 30 minutes 19 g of 4-bromobutyric acid ethyl ester are added dropwise. Stirring is continued overnight at 70° C and the mixture is then left to stand for 2 days at room temperature and is evaporated to dryness under reduced pressure. The evaporation residue is distributed 3 times between 200 ml of ether and 200 ml of water in each case. The organic phases are combined, dried over sodium sulphate and evaporated to dryness under reduced pressure. This gives 4-[p-(1-cyclooctenyl)-phenoxy]-butyric acid ethyl ester.

EXAMPLE 2

50 ml of 2 N sodium hydroxide solution are added to a solution of 21 g of crude 4-[p-(1-cyclooctenyl)-phenoxy]-butyric acid ethyl ester in 300 ml of ethanol, whilst stirring, and the mixture is stirred for 48 hours and evaporated to dryness under reduced pressure. The evaporation residue is distributed 3 times between 200 ml of ether and 200 ml of water in each case and the water phases are acidified to pH = 2 with concentrated hydrochloric acid and extracted with 3 times 200 ml of ether. The resulting organic phases are combined, washed until neutral, dried over sodium sulphate and evaporated under reduced pressure. The evaporation residue, after treatment with active charcoal and crystallisation from ether-petroleum ether, gives 4-[p-(1- cyclooctenyl)-phenoxy]-butyric acid in the form of white needles of melting point 110°–111° C.

EXAMPLE 3

Following an analogous procedure to that described in Examples 1 and 2, but starting from p-(1-cyclohexenyl)-phenol and 4-bromobutyric acid ethyl ester, 4-[p-(1-cyclohexenyl)-phenoxy]-butyric acid of melting point 123°–125° C (from ether) is obtained.

EXAMPLE 4

Following an analogous procedure to that described in Examples 1 and 2, m-cyclohexylphenol and 4-bromobutyric acid ethyl ester give 4-(m-cyclohexylphenoxy)-butyric acid of melting point 83°–84° C (from hexane).

EXAMPLE 5

10.0 g of p-(1-cyclohexenyl)-phenol are added to a solution of 1.5 g of sodium in 70 ml of absolute ethanol whilst stirring in an anhydrous atmosphere, and the mixture is stirred for a further 30 minutes and evaporated to dryness under reduced pressure. For complete removal of the ethanol, the residue is evaporated 3 times with 50 ml of absolute benzene at a time and is dried in a high vacuum. The dry residue is taken up in 50 ml of absolute dimethylformamide, 8.0 g of propanesultone are added whilst stirring and the mixture is stirred overnight at 80° C and is evaporated to dryness under reduced pressure (finally in a high vacuum). The residue is suspended in 200 ml of ether and 50 ml of ethanol and filtered off. The filter residue is thoroughly washed with ether, dried and recrystallised from water. This gives the sodium salt of 3-[p-(1-cyclohexenyl)-phenoxy]-propanesulphonic acid in the form of mica-like flakes of melting point > 300° C.

EXAMPLE 6

15 g of p-(1-cyclohexenyl)-thiophenol are added to a solution of 2.08 g of sodium in 70 ml of absolute ethanol whilst stirring in an anhydrous atmosphere, and after 30 minutes 12.2 g of propanesultone are added and the mixture is warmed overnight to 80° C. It is then evaporated in vacuo to ⅛ of its volume and the residue is distributed between 1,000 ml of water and 200 ml of ether. The aqueous phase is separated off, warmed slightly and filtered through kieselguhr. The filtrate is warmed gently and is concentrated by approx. 200 ml under reduced pressure. On leaving it to stand, the sodium salt of 3-[p-(1-cyclohexenyl)-phenylthio]-propanesulphonic acid of melting point > 270° C crystallises out.

The starting material can be obtained as follows:

23.7 g of p-(1-cyclohexenyl)-bromobenzene (C.A. 28, 140³) in 50 ml of absolute tetrahydrofurane and 100 ml of absolute ether are added dropwise, whilst excluding water and stirring, to 2.64 g of magnesium filings covered with a little absolute tetrahydrofurane. After completion of the addition, stirring is continued at 30° C until practically all the magnesium is in solution. 3.04 g of sulphur are added in portions to the reaction mixture under nitrogen and stirring is then continued for one hour at room temperature. The reaction mixture is then acidified with 2.5 N hydrochloric acid in a nitrogen atmosphere at 0° C whilst stirring and is extracted with twice 100 ml of ether. The combined ether extracts are then extracted with five times 80 ml of 2 N sodium hydroxide solution under nitrogen at 0° C. The aqueous phase is adjusted to pH = 5 with concentrated hydrochloric acid whilst cooling with ice, and is extracted with ether. The organic phase is washed with saturated sodium chloride solution, dried over sodium sulphate and evaporated to dryness in vacuo at room temperature. Crude p-(1-cyclohexenyl)-thiophenol, which can be further converted direct, without additional purification, is obtained in the evaporation residue.

EXAMPLE 7

12 g of p-(1-cyclooctenyl)-phenol are first added to a solution of 1.7 g of sodium in 60 ml of absolute ethanol whilst stirring in an anhydrous atmosphere, and after 30 minutes 18.8 g of 5-bromopentanoic acid ethyl ester are added dropwise. After completion of the addition, the mixture is stirred for 15 hours at 70° C and is evaporated to dryness in vacuo. The evaporation residue is distributed between 3 times 150 ml of ether and twice 100 ml of water. The organic phases are combined, dried over sodium sulphate and evaporated in vacuo. Chromatography of the evaporation residue on silica gel with chloroform as the eluant gives 5-[p-(1-cyclooctenyl)-phenoxy]-pentanoic acid ethyl ester of boiling point 165°–170° C at 0.03 mm Hg.

EXAMPLE 8

20 ml of 2 N sodium hydroxide solution are added to a solution of 15 g of 5-[p-(1-cyclooctenyl)-phenoxy]-pentanoic acid ethyl ester in 150 ml of ethanol and the mixture is left to stand at room temperature for 48 hours. It is then evaporated in vacuo to a volume of about 30 ml and the evaporation residue is distributed, at 5° C, between 100 ml of 2 N hydrochloric acid and twice 200 ml of ether. The organic phases are washed until neutral, dried over sodium sulphate and evaporated in vacuo. Crystallisation of the evaporation residue from ether-petroleum ether gives 5-[p-(1-cyclooctenyl)-phenoxy]-pentanoic acid of melting point 94–96° C.

EXAMPLE 9

2 g of palladium on charcoal (5% strength) are added to a solution of 20 g of 5-[p-(1-cyclooctenyl)-phenoxy]-pentanoic acid ethyl ester in 100 ml of ethanol and hydrogenation is carried out at room temperature and normal pressure until one equivalent of hydrogen has been absorbed. The catalyst is then filtered off and the filtrate is evaporated to dryness in vacuo. Distillation of the evaporation residue in a high vacuum gives 5-(p-cyclooctyl-phenoxy)-pentanoic acid ethyl ester of boiling point 170°–175° C at 0.05 mm Hg.

EXAMPLE 10

Analogously to the method described in Example 7, using 11.8 g of 5-(p-cyclooctyl-phenoxy)-pentanoic acid ethyl ester as the starting material gives 5-(p-cyclooctylphenoxy)-pentanoic acid of melting point 79°–80° C (from ether-petroleum ether; needles).

EXAMPLE 11

1 g of palladium on charcoal (5% strength) is added to a solution of 9.5 g of 4-[p-(1-cyclooctenyl)-phenoxy]-butyric acid in 150 ml of dioxane and hydrogenation is carried out at room temperature and normal pressure until one equivalent of hydrogen has been absorbed. The catalyst is then filtered off, the filtrate is evaporated to dryness in vacuo and the evaporation residue is recrystallised from ether-petroleum ether. This gives 4-(p-cyclooctyl-phenoxy)-butyric acid of melting point 127°–128° C.

EXAMPLE 12

Analogously to the process described in Example 1, using 13.2 g of p-(1-cycloheptenyl)-phenol and 21.1 g of 4-bromobutyric acid ethyl ester as starting material gives crude 4-[p-(1-cycloheptenyl)-phenoxy]-butyric acid ethyl ester of boiling point 160° C at 0.03 mm Hg, after chromatography on silica gel with methylene chloride as the eluant and subsequent fractional distillation in a high vacuum.

EXAMPLE 13

Analogously to the process described in Example 2, using 9.7 g of 4-[p-(1-cycloheptenyl)-phenoxy]-butyric acid ethyl ester as the starting material gives 4-[p-(1-cycloheptenyl)-phenoxy]-butyric acid of melting point 87°–88° C (from ethanol-water).

EXAMPLE 14

Tablets containing 10 mg of active compound can be manufactured to have, for example, the following composition:

| Composition | |
|---|---|
| 4-[p-(1-cyclooctenyl)-phenoxy]-butyric acid | 10.0 mg |
| Wheat starch | 29.5 mg |
| Lactose | 50.0 mg |
| Colloidal silica | 5.0 mg |
| Talc | 5.0 mg |
| Magnesium stearate | 0.5 mg |
| | 100.0 mg |

MANUFACTURE

The 4-[p-(1-cyclooctenyl)-phenoxy]-butyric acid is mixed with a part of the wheat starch, with lactose and with colloidal silica and the mixture is forced through a sieve. A further part of the wheat starch is worked to a paste with a 5-fold amount of water on a water bath and the powder mixture is kneaded with this paste until a slightly plastic mass has been produced.

The plastic mass is pressed through a sieve of approx. 3 mm mesh width and dried and the dry granules are again forced through a sieve. The remaining wheat starch, talc and magnesium stearate are then admixed and the resulting mixture is pressed to give tablets weighing 100 mg.

We claim:

1. A compound of the general formula I

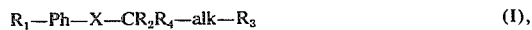

$$R_1-Ph-X-CR_2R_4-alk-R_3 \qquad (I),$$

wherein $R_1$ denotes cycloalkyl or 1-cycloalkenyl with 5 to 8 ring members, Ph denotes o- m- or p-phenylene, unsubstituted or monosubstituted by lower alkyl, lower alkoxy or halogen, X denotes the oxy or thio group, $R_2$ denotes hydrogen or alkyl with 1 to 4 C atoms, $R_4$ is hydrogen or, if $R_1$ is 1-cycloalkenyl, it is also alkyl with 1 to 4 C atoms, $R_3$ denotes carboxyl or carboxyl esterified by a lower alkanol, cycloalkanol or phenylalkanol, and $CR_2R_4$-alk denotes alkylene with 4 to 11 C atoms, straight or branched in the α-position to the group X, which separates the groups X and $R_3$ by 4 to 11 carbon atoms, or a therapeutically acceptable salt thereof.

2. A compound as claimed in claim 1, of the formula I, wherein $R_1$, $R_2$, $R_3$, $R_4$, Ph, X and alk have the meaning given in claim 1, but the moiety $CR_2R_4$-alk separates the groups X and $R_3$ by 4 to 7 C atoms, or a therapeutically acceptable salt thereof.

3. A compound as claimed in claim 1 of the formula I, wherein $R_1$ denotes cyclooctyl, cycloheptyl, cyclohexyl, cyclopentyl, 1-cyclooctenyl, 1-cycloheptenyl, 1-cyclohexenyl or 1-cyclopentenyl, Ph denotes o-, m- or p-phenylene unsubstituted or monosubstituted by methoxy, methyl or chlorine, X denotes the oxy or thio group, $CR_2R_4$-alk separates the groups X and $R_3$ by 4 to 7 carbon atoms and denotes alkylene with 4 to 7 C atoms which is optionally branched once in the α-position to the group X and $R_3$ denotes free carboxyl or carboxyl esterified with a lower alkanol, or a therapeutically acceptable salt thereof.

4. A compound as claimed in claim 1 of the formula I, wherein $R_1$ denotes 1-cyclooctenyl, 1-cycloheptenyl, cycloheptyl, 1-cyclohexenyl or cyclohexyl, Ph denotes unsubstituted m- or p-phenylene, X denotes the oxy group or thio group, $R_2$ and $R_4$ denote hydrogen, alk denotes ethylene and $R_3$ denotes the free carboxyl group, or a therapeutically acceptable salt thereof.

5. A compound as claimed in claim 1 of the formula 1, wherein $R_1$ denotes cyclooctyl, 1-cyclooctenyl, cycloheptyl, 1-cycloheptenyl, cyclohexyl or 1-cyclohexenyl, Ph denotes p-phenylene, X denotes the oxy group, $CR_2R_4$-alk denotes unbranched alkylene which separates the group X and $R_3$ by 4 to 7 C atoms, and $R_3$ denotes carboxyl or carboxyl esterified with a lower alkanol with 1 to 4 C atoms, or a therapeutically acceptable salt thereof.

6. A compound as claimed in claim 1 being 4-[p-(1-Cyclohexenyl)-phenoxy]-butyric acid or a therapeutically acceptable salt thereof.

7. A compound as claimed in claim 1 being 4-[p-(1-Cyclooctenyl)-phenoxy]-butyric acid or a therapeutically acceptable salt thereof.

8. A compound as claimed in claim 1 being 4-(m-Cyclohexylphenoxy)-butyric acid or a therapeutically acceptable salt thereof.

9. A compound as claimed in claim 1 being 5-[p-(1-Cyclooctenyl)-phenoxy]-n-pentanoic acid or a therapeutically acceptable salt thereof.

10. A compound as claimed in claim 1 being 5-(p-Cyclooctenylphenoxy)-n-pentanoic acid or a therapeutically acceptable salt thereof.

11. A compound as claimed in claim 1 being 4-[p-(1-Cyclooctenyl)-phenoxy]-butyric acid or a therapeutically acceptable salt thereof.

12. A compound as claimed in claim 1 being 4-(p-Cyclooctylphenoxy)-butyric acid or a therapeutically acceptable salt thereof.

13. A compound as claimed in claim 1 being 4-[p-(1-Cycloheptenyl)-phenoxy]-butyric acid ethyl ester or a therapeutically acceptable salt thereof.

14. A compound as claimed in claim 1 being 4-[p-(1-Cycloheptenyl)-phenoxy]-butyric acid or a therapeutically acceptable salt thereof.

* * * * *